United States Patent [19]

Gullberg et al.

[11] Patent Number: 5,210,421
[45] Date of Patent: May 11, 1993

[54] SIMULTANEOUS TRANSMISSION AND EMISSION CONVERGING TOMOGRAPHY

[75] Inventors: Grant T. Gullberg, Salt Lake City, Utah; Hugh T. Morgan, Highland Heights, Ohio; Chi-Hua Tung, Salt Lake City, Utah; Gengsheng L. Zeng, Salt Lake City, Utah; Paul E. Christian, Salt Lake City, Utah

[73] Assignee: Picker International, Inc., Highland Hts., Ohio

[21] Appl. No.: 712,676

[22] Filed: Jun. 10, 1991

[51] Int. Cl.5 .............................................. G01T 1/166
[52] U.S. Cl. ................................................. 250/363.04
[58] Field of Search ..................................... 250/363.04

[56] References Cited

U.S. PATENT DOCUMENTS 4,670,657 6/1987 Hawman et al. .................. 250/505.1
5,055,687 10/1991 Ichihara .......................... 250/363.09

FOREIGN PATENT DOCUMENTS 9100048 1/1991 World Int. Prop. O. ...... 250/363.04

Primary Examiner—Constantine Hannaher
Attorney, Agent, or Firm—Fay, Sharpe, Beall, Fagan, Minnich & McKee

[57] ABSTRACT

A SPECT system includes three gamma camera heads (22a), (22b), (22c) which are mounted to a gantry (20) for rotation about a subject (12). The subject is injected with a source of emission radiation, which emission radiation is received by the camera heads. A reconstruction processor (112) reconstructs the emission projection data into a distribution of emission radiation sources in the subject. Transmission radiation from a radiation source (30) passes through the subject and is received by one of the camera heads (22a) concurrently with the emission radiation. The transmission radiation data is reconstructed into a three-dimensional CT type image representation of radiation attenuation characteristics of each pixel of the subject. An attenuation correction processor (118) corrects the emission projection data to compensate for attenuation along the path or ray that it traversed. In this manner, an attenuation corrected distribution of emission sources is generated.

24 Claims, 7 Drawing Sheets

SIMULTANEOUS TRANSMISSION AND EMISSION CONVERGING TOMOGRAPHY

BACKGROUND OF THE INVENTION

The present invention relates to the art of diagnostic imaging. It finds particular application in conjunction with single-photon emission computed tomography (SPECT) with multi-headed cameras and will be described with particular reference thereto. It is to be appreciated, however, that the invention will also find application in other non-invasive investigation techniques such as positron emission tomography (PET) and other diagnostic modes in which a subject is examined for emitted radiation.

Heretofore, single photon emission computed tomography has been used to study the radionuclide distribution in subjects. Typically, one or more radiopharmaceuticals were injected into a patient. The radiopharmaceuticals were commonly injected into the patient's blood stream for imaging the circulatory system or for imaging specific organs which absorb the injected radiopharmaceuticals. Gamma or scintillation camera heads were placed closely adjacent to a surface of the patient to monitor and record emitted radiation. In single photon-emission computed tomography, the head was rotated or indexed around the subject to monitor the emitted radiation from a plurality of directions. The monitored radiation data from the multiplicity of directions was reconstructed into a three dimensional image representation of the radiopharmaceutical distribution within the patient.

One of the problems with the SPECT imaging technique is that photon absorption and scatter by portions of the subject between the emitting radionuclide and the camera head distorted the resultant image. One solution for compensating for photon attenuation was to assume uniform photon attenuation throughout the subject. That is, the patient was assumed to be completely homogenous in terms of radiation attenuation with no distinction made for bone, soft tissue, lung, etc. This enabled attenuation estimates to be made based on the surface contour of the subject. Of course, human subjects do not cause uniform radiation attenuation, especially in the chest.

In order to obtain more accurate radiation attenuation measurements, a direct measurement was made using transmission computed tomography techniques. That is, radiation was projected from a radiation source to the patient and radiation that was not attenuated was received by detectors at the opposite side. The source and detectors were rotated to collect data through a multiplicity of angles. This data was reconstructed into an image representation using conventional tomography algorithms. The radiation attenuation properties of the subject from the transmission computed tomography image were used to correct for radiation attenuation in a later SPECT or other emission study.

One of the problems with this two step technique resided in registering the transmission computed tomography and the SPECT or other emission study images. Any misalignment of the two images provided erroneous radiation attenuation information which impaired the diagnostic value of the reconstructed images. Registration was improved by using discrete extrinsic or intrinsic landmarks that were known to bear a constant relationship to the patient's anatomy during the two studies. Another technique was to use a three dimensional surface identification algorithm to construct numerical models of the external surface of the images. The numerical models were then translated, rotated, and descaled until an optimal match was found. Nonetheless, there was still significant uncertainty when combining images from different modalities. Moreover, inconvenience, cost, and double scan time were inevitable when obtaining scans from two modalities.

To overcome these disadvantages, simultaneous transmission and emission data acquisition was utilized. The gamma camera head was positioned on one surface of the subject and a large plane of a radiation source was disposed opposite the camera head, e.g. between the subject and a counterweight for the camera head. The patient was injected with a different radionuclide from the radionuclide in the large planar source. Using conventional dual radionuclide technology, the data from the injected or emitted radionuclide and the data from the larger planar source or transmitted radiation were separated. The transmitted data was reconstructed using parallel ray transmitted computed tomography algorithms to produce attenuation correction coefficients for use in the emitted radiation reconstruction.

One problem with using a large planar source resided in its large bulk and weight. The large size of the planar source prevented the use of systems with multiple gamma cameras. Another drawback was the poor counting statistics of parallel-beam geometry reconstructions. Stronger radiation sources could be utilized to compensate for the poor counting statistics, but the associated higher patient radiation exposures are undesirable.

The present invention contemplates a new and improved simultaneous transmission and emission tomography method and apparatus which overcomes the above-referenced problems and others.

SUMMARY OF THE INVENTION

In accordance with one aspect of the present invention, a simultaneous transmission and emission tomography system is provided. Three or more gamma cameras are mounted at about regular intervals around a subject that is to receive an emission radionuclide. An external radiation source is disposed opposite at least one of the gamma cameras and generally between the other two. A first algorithm means processes the transmission radiation detected by the first gamma camera to generate attenuation correction coefficients therefrom. A second algorithm means reconstructs emission radiation received by the gamma cameras into an image representation using the attenuation correction coefficients to correct for radiation attenuation.

In accordance with another aspect of the present invention, a method of reconstructing emission projection signals from a three head SPECT system is provided. Sets of transmission and emission projection signals are collected. The transmission and emission projection signals are corrected for energy window cross-talk. The transmission projection signals are reconstructed into a set of attenuation coefficients. The emission projection signals and the attenuation coefficients are reconstructed to produce an image space estimate of a distribution of the emission radionuclide in pixel space which is compensated, at least in part, for the attenuation of the subject.

In accordance with more limited aspects of the method, the transmission projection signals are collected by a camera head which receives radiation through a collimator from an oppositely disposed radiation source. The radiation source and collimator combination may include a line source with fan collimator, a rectangular source with fan collimator, a point source with cone collimator, a disk source with cone collimator, a line source with astigmatic collimator which can be placed at two different focal lines, a flood source with parallel collimator, or a general source with arbitrary collimator geometry. Moreover, the projection source may be a radionuclide, an x-ray tube, or the like.

In accordance with other more limited aspects of the present invention. Transmission and emission data collected by the camera heads are corrected for the effects of scattered radiation and other photopeaks.

In accordance with another aspect of the present invention, a method of simultaneously measuring transmission and emission projection data from transmission and emission sources of different energies is provided. Energy windows for the transmission and emission energy sources are set. The transmission source is set such that incident transmission photons are projected only on a first gamma camera head. At least one of the transmission data detected by the first head and emission data detected by the first, second, and third heads is subtractively corrected.

In accordance with another aspect of the present invention, a method of simultaneously measuring transmission and emission projection data for transmission and emission sources of the same energy is provided. A transmission energy source is disposed such that incident transmission photons are projected only on to a first head. Emission data collected by other gamma camera heads is corrected for absorption, scatter and other photopeak with data derived from the transmission photons detected by the first head.

In accordance with another aspect of the present invention, a method of correcting for attenuation using a truncated transmission scan is provided. Emission projection data and truncated transmission projection data are obtained. The transmission projection data is reconstructed using a reconstruction algorithm which solves a system of linear equations. From the reconstructed, truncated transmission data, attenuation factors are determined. The emission projection data is reconstructed correcting for attenuation using the attenuation factors determined from the reconstructed truncated transmission data.

One advantage of the present invention is that it accurately and efficiently produces attenuation corrected emission radiation data reconstruction.

Another advantage of the present invention is that it concurrently collects the emission data and the transmission correction data.

Still further advantages will become apparent to those of ordinary skill in the art upon reading and understanding the following detailed description.

BRIEF DESCRIPTION OF THE DRAWINGS

The invention may take form in various steps and arrangements of steps and in various components and arrangements of components. The drawings are only for purposes of illustrating the preferred embodiment and are not to be construed as limiting the invention.

DETAILED DESCRIPTION OF THE PREFERRED EMBODIMENT

Figure 1:
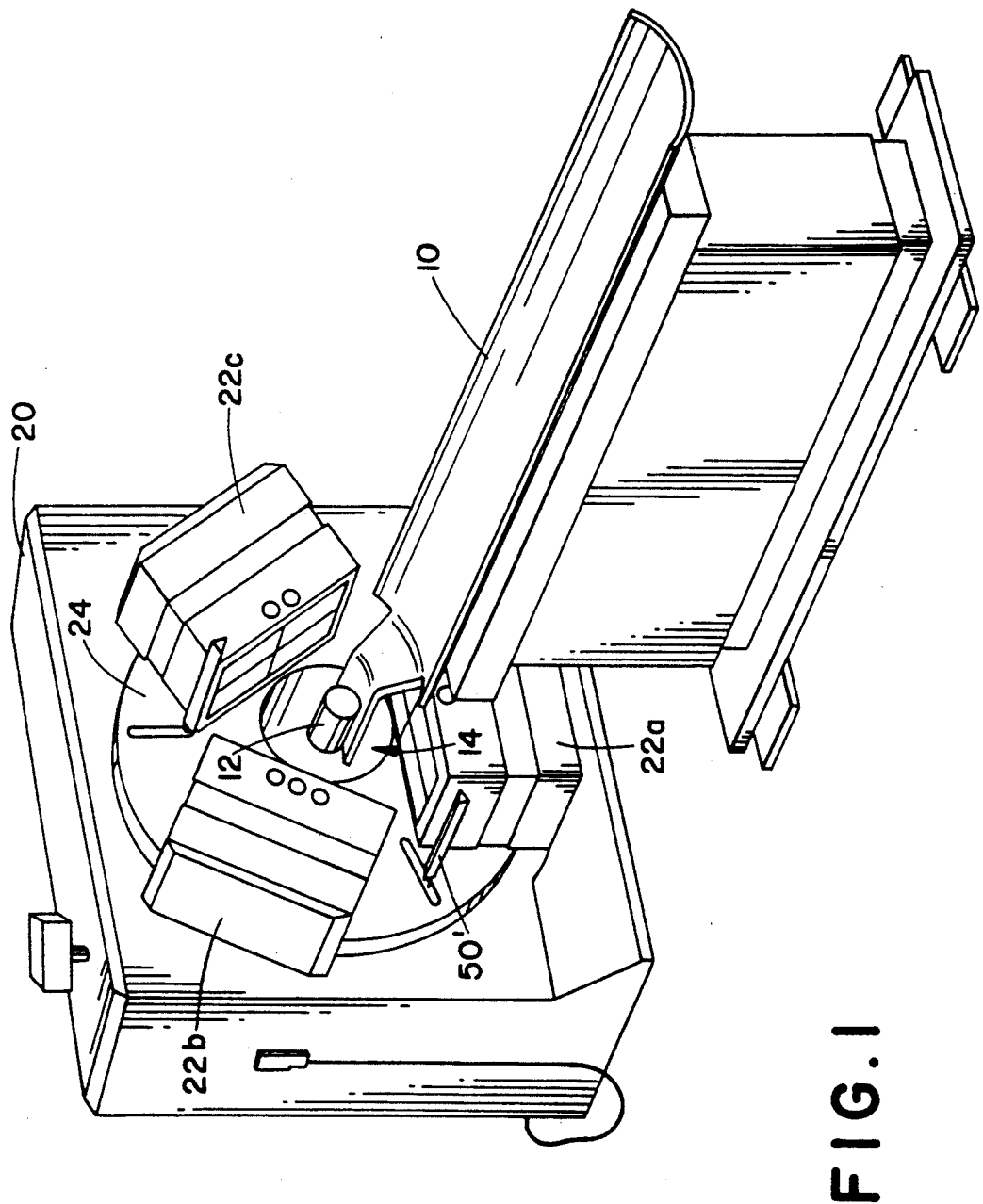
FIG. 1 is a prospective view of a gamma camera system in accordance with the present invention.

With reference to FIG. 1, a SPECT camera assembly includes a patient couch or support means 10 for holding subject such as a phantom 12 or a human patient in an examination region 14.

Figure 2:
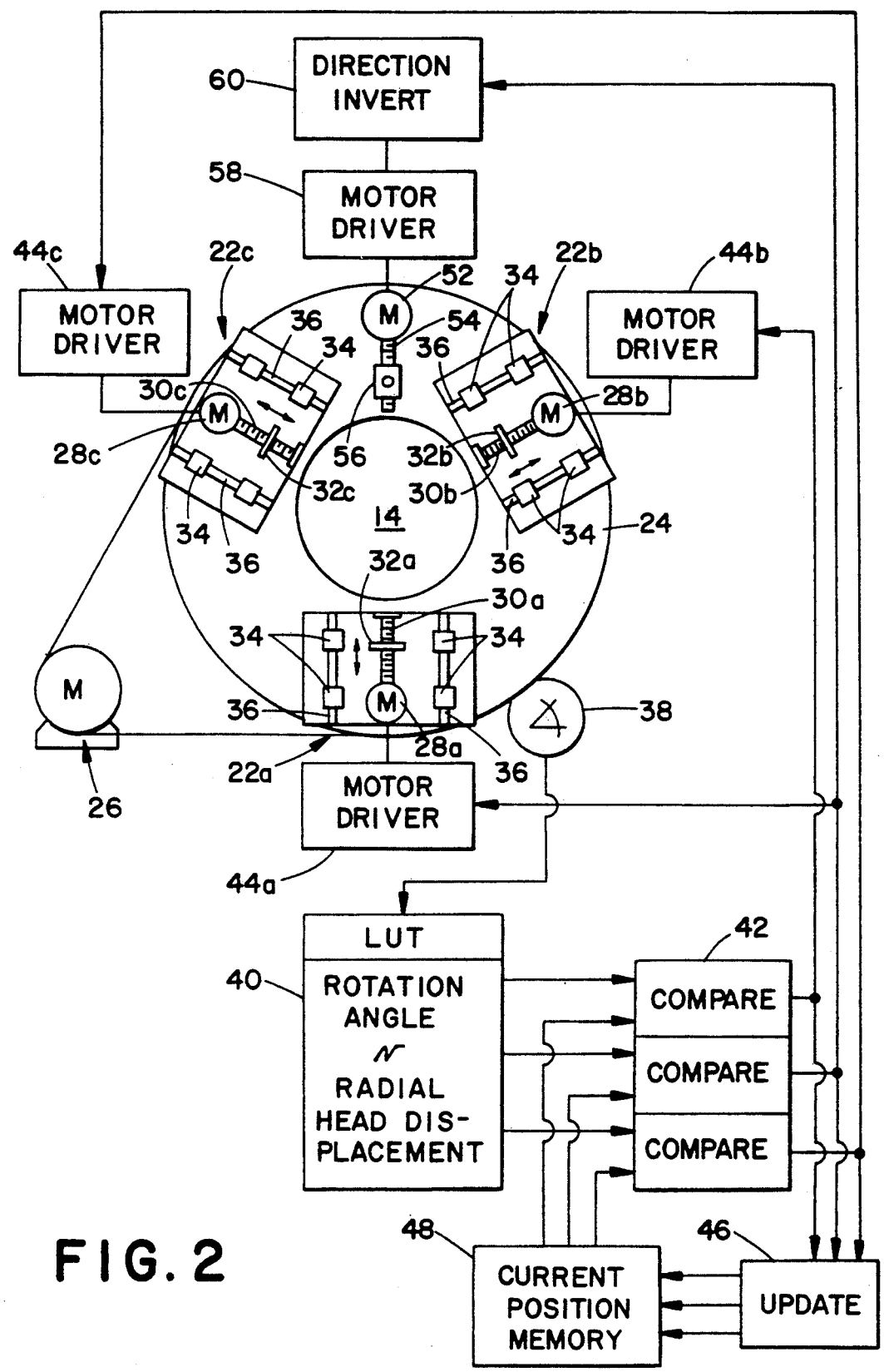
FIG. 2 is a diagrammatic view of a gamma camera head and transmission source position controller.

With continuing reference to FIG. 1 and further reference to FIG. 2, a gantry 20 supports a plurality of gamma camera heads 22a, 22b, and 22c at regular intervals around the examination region 14, e.g. 120°. More specifically, a rotating means including a rotating drum or face plate 24 to which the camera heads are mounted and a drive motor 26 selectively rotate the camera heads around the examination region. Linear drive means, such as motors 28a, 28b, 28c that rotate screw driver 30a, 30b, 30c, that engage followers 32a, 32b, 32c, are mounted on the reverse side of the face plate for selectively moving each gamma camera head on roller carriages 34a along tracks or guides 36 radially toward and away from the subject.

A control means is provided for rotating the camera heads around the subject and moving the camera heads toward and away from the subject during the rotation, as is conventional in the art. More specifically, an angular position detector 38 detects the number of degrees of rotation of the plate 24 from an arbitrary 0° origin. A look-up table 40 is loaded with one of a plurality of selectable orbits e.g. an oval orbit of a preselected size which most closely matches the patients size. The look-up table 40 is addressed by the monitored angle to retrieve the radial distance from the center of the examination region for each camera head at that angle. A comparing means 42 compares the desired radial distance from the look-up table with the actual, current radial distance of each head. The difference is conveyed to drivers 44a, 44b, 44c which cause corresponding linear motors 28a, 28b, 28c to move the heads the corresponding physical distance. A memory update means 46 add/subtracts the distance differences with the corresponding radial position of each head in a current position memory 48. This enables the camera heads to move around the subject in a circular path, an elliptical path, a peanut-shaped path, or other orbits by merely reloading the look-up table 40 from a large memory, such as a disc (not shown), of precalculated orbits. The symmetry in a circular path facilitates reconstruction of the collected data; whereas, the elliptical and peanut orbits move the gamma camera heads closer to the patient improving image quality.

A radiation source 50, a line source in the FIG. 1 embodiment, is mounted directly opposite a first of the gamma camera heads 22a and between the other two gamma camera heads 22b, 22c. The radiation source is selectively positionable radially either closer to or further from the first camera head 22a. Preferably, the radiation source is disposed behind a plane of the face of the camera heads 22b and 22c such that radiation therefrom cannot impinge directly on the other camera heads 22b, 22c. A collimating or shield means 51 is mounted to the radiation source to limit the projection of radiation to a fan beam that intercepts the first gamma camera head 22a. Optionally, one or more additional radiation sources 50' may also be provided. The transmission radiation source may be a tube or vessel filled with a radionuclide or an active radiation generator such as an x-ray tube.

A motor 52 rotates a screw 54 that moves a follower 56 which is mounted to move the radiation source radially. Preferably the control circuit controls the motor 52 such that the radiation source 50 and the first camera head 22a stay a fixed distance apart. Direction invertor means 60 reverses the sign or direction of movement such that a driver 58 causes the motor 52 to move the radiation source the same distance, but in the opposite radial direction relative to the center of the examination region as the driver 44a causes the motor 28a to move the first head 22a. Alternately, the transmission radiation source 50 may be mounted to one of the adjoining heads 22b or 22c. Because movement of either head radially changes the effective angle of the fan, the reconstruction algorithm is adjusted with angular position to accommodate the changing effective fan angle. The effective fan angle is preferably precalculated and stored in the look-up table 40.

As is conventional in the art, each camera head has a scintillation crystal that responds to incident radiation by producing a flash of light. An array of photomultiplier tubes produce electrical signals in response to each flash of light. The signals responsive to the same scintillation or flash of light are combined. The magnitude of the resultant sum is indicative of the energy of the incident radiation and the relative response of the closest photo-multiplier tubes is indicative of the spatial location of the scintillation.

Figure 3:
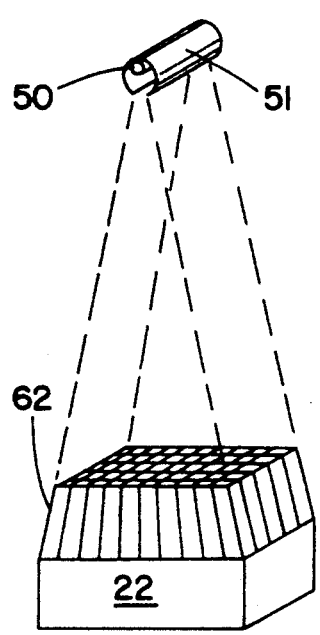
FIG. 3 is a diagrammatic illustration of a line source, gamma camera head, and fan beam collimator.
Figures 4A, 4B:
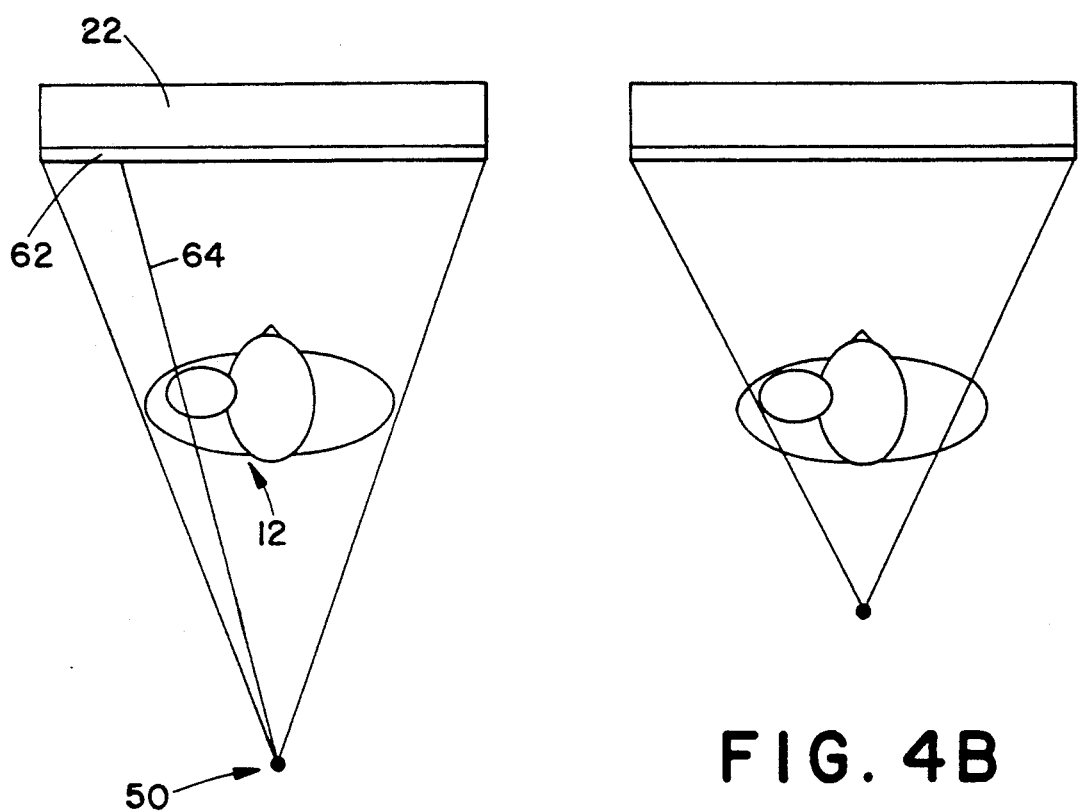
FIGS. 4A and 4B are diagrammatic illustrations of a non-truncated and a truncated transmission scan.

With reference to FIG. 3, collimator 62, limit each incremental area of the scintillation crystal receiving radiation from along a fixed direction or ray, e.g. ray 64 of FIG. 4A. The collimator has a plurality of vanes 66 which are directed toward a focal point, typically the transmission radiation source 50. The vanes are sufficiently long that radiation impinging on the corresponding detector head is limited to radiation coming along a ray substantially from the focal point. In a preferred embodiment, the focal point and head size are selected such that a patient or subject under examination is completely encompassed within the transmission radiation fan as illustrated in FIG. 4A.

Conventional gamma camera heads can image radiation in two or more energy windows or ranges simultaneously. In a conventional dual energy gamma camera head, the sum signals are sorted based on amplitude. More specifically, energy windows or ranges are defined. Each window corresponds to a photopeak or energy spectrum of a radionuclide to be used in the examination. In the preferred embodiment, the injected or emission radionuclide has one preselected energy and the radiation source 50 or transmissive radiation has a second different energy. In this manner, the camera heads separate the transmission and emission radiation data by using the conventional energy separation circuitry used during dual injected radiopharmaceutical examinations. A position resolver resolves the position on the crystal, hence the ray angle, corresponding to scintillations or radiation events within one of the energy windows.

Figure 5A:
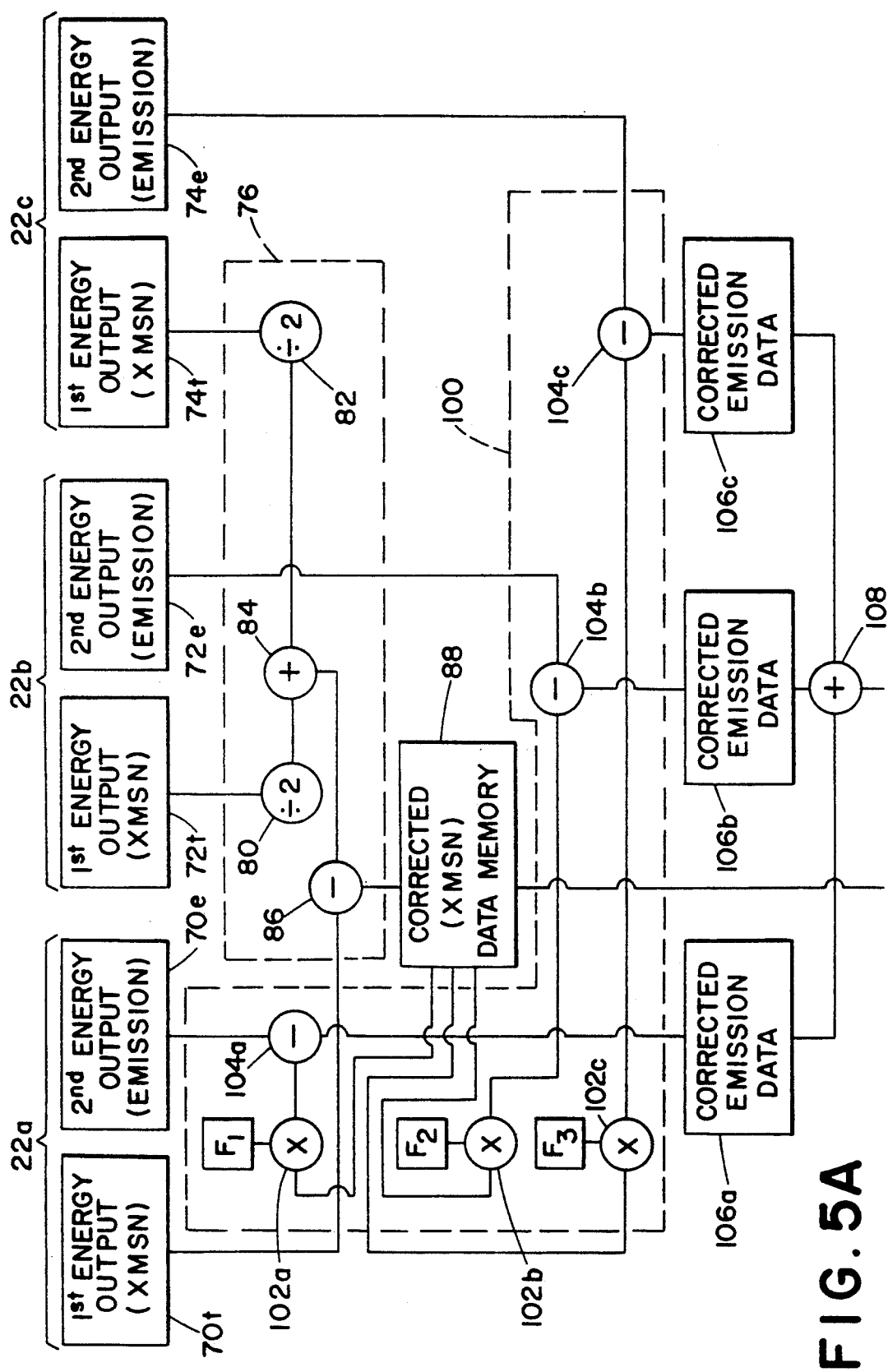
FIGS. 5A and 5B illustrate the technique for processing the emission and transmission data in different energy ranges collected with the camera system of FIG. 1.
Figure 5B:
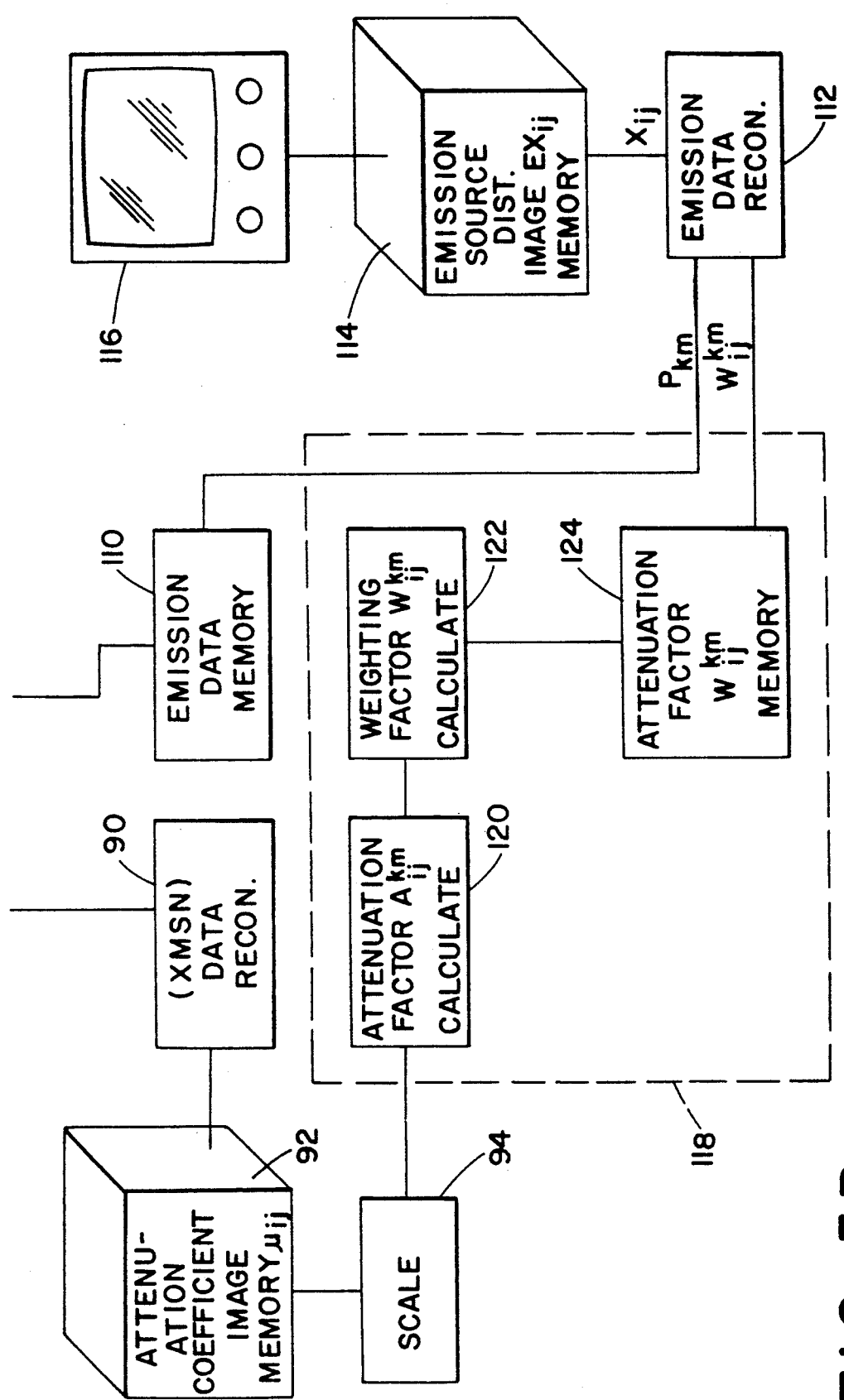

With reference to FIGS. 5A and 5B, the first head 22a has first energy level output means 70t for separating and outputting location or ray signals for each scintillation with an energy in the range of the transmission source 50 and a second energy level output means 70e for separating and outputting location or ray signals for each scintillation in the energy range of the emission radionuclide. Although the second head 22b and the third head 22c do not receive the transmission radiation directly, they do receive some of the transmission radiation by scattering and photons from other photopeak(s) of the emission source. Accordingly, the second head 22b has a transmitted energy output means 72t for separating and outputting transmission energy range data and the third head 22c has a transmitted energy output means 74t for transmission energy range data. A transmission radiation data correction means 76 corrects the transmission energy data from the output means 70t for emission radiation photopeak(s) in the transmission energy range.

The transmission radiation correction means 76 includes a pair of dividers 80 and 82 which divide the output signals 72t and 74t in half, respectively. A summing means 84 sums these two half signals to provide a signal which is effectively the average of other emission photopeak photons received by heads 22b and 22c. A subtracting means 86 subtracts the average number of photons from the emission source detected in the transmission energy range by heads 22b and 22c from the transmission energy signals from head 22a. A corrected transmission projection data memory 88 stores the corrected transmission projection data.

A transmission reconstruction means 90 reconstructs the transmission radiation data with a conventional CT or iterative reconstruction algorithm into a three dimensional electronic image representation stored in a three dimensional transmission radiation or attenuation image memory 92, e.g. a fan beam reconstruction algorithm. Each pixel or voxel of the attenuation image memory 92 represents the radiation attenuation by a corresponding pixel or voxel of the examination region 14 or the subject being examined. Thus, when an emission radiation event occurs at a given pixel or voxel, one can determine the amount of radiation attenuation along the rays between the event voxel and the points on each head at which the scintillation occurs by summing the attenuation values of each pixel or voxel through which the ray passes. The attenuation probability of detection is the exponentiation of the negative of this sum. A further correction can be made by determining the distance through each intervening pixel or voxel the ray passes. When the ray extends through a pixel or voxel squarely from one face to the opposite face, the entire attenuation value is added. If the path goes through only a small corner, a correspondingly smaller portion of the attenuation value is added. A scaling means 94 adjusts the attenuation data in accordance with the relative energy of the transmission and emission sources, e.g. the ratio or a non-linear relationship of energy.

A major goal in transmission CT is to compute local attenuation coefficients for the object of interest. The recorded projection data in a transmission scan is converted to an appropriate form by taking the natural logarithm of the ratio of unattenuated acquired count per pixel or voxel (flood image $N_0$) to observed count at a given pixel (recorded projection N). For those regions with observed count greater than the flood image, the line integral of the attenuation coefficients is set equal to zero, i.e.:

$$N = N_0 \times e^{-\mu x}. \quad (1a)$$

$$\text{projection} = \int \mu dx = \ln\left(\frac{N_0}{N}\right) \quad \text{if } N \leq N_0 \quad (1b)$$

$$\text{projection} = 0 \quad \text{if } N > N_0. \quad (1c)$$

After performing this conversion, a conventional CT or iterative reconstruction algorithm is used to obtain the map of attenuation coefficients $\mu_{ij}$. The calculated attenuation map is used to correct for the photon attenuation in the emission study.

By way of a specific example of the scaling means 94 in which scales the attenuation coefficients $\mu_{ij}^{Tl}$ of a 75 kev Tl-201 emission source relative to the attenuation coefficients $\mu_{ij}^{TC}$ of a 140 kev TC-99m transmission source, the attenuation coefficients $\mu_{ij}^{Tl}$ for Tl-201 emission is approximated by:

$$\mu_{ij}^{Tl} = \frac{\mu_{75kev}}{\mu_{140kev}} \times \mu_{ij}^{TC} = \frac{0.184/\text{cm}}{0.153/\text{cm}} \times \mu_{ij}^{TC} = 1.2\mu_{ij}^{TC}. \quad (2)$$

Another scaling method is applied to the higher energy (140 kev) attenuation map. This method uses a look-up table of the linear attenuation coefficients for different materials at both 75 kev and 140 kev. A data interpolation technique is used to determine the scaling factor to transform the attenuation distribution at 140 kev to that at 75 kev.

The second head similarly has an emission energy location or ray signal output means 72e and the third head 22c has an emission energy ray signal output 74e. Some of the transmission photons and scattered emission photons are detected within the emission radiation energy range. An emission radiation correction means 100 removes the component of the measured emission radiation which is attributable to the transmission radiation. The emission radiation correcting means 100 includes a first multiplying means 102a for multiplying the corrected first detector head transmission radiation signal from memory 88 by a scaling factor $F_1$. A second multiplying means 102b multiplies the corrected transmission radiation signal corresponding to the first detector head from the corrected transmission data memory 88 by a second scaling factor $F_2$ and a third multiplying means 102c multiplies the corrected transmission signal from the memory 88 by a third scaling factor $F_3$.

The scaling factors $F_1$, $F_2$, $F_3$ are determined from initial calibration tests. The tests begin with collecting pure transmission data using a cold phantom, i.e. no emission source. The correction factors $F_1$, $F_2$, $F_3$ are determined for each head by calculating a ratio of the counts in the emission and transmission energy windows or ranges. Subtraction circuits 104a, 104b, 104c subtract the product of the transmission radiation value and the corresponding correction factor from the actual measured emission radiation projection data. Corrected emission ray or location signal memories 106a, 106b, and 106c store the corrected emission projection data from heads 22a, 22b, 22c, respectively. A combining circuit 108 combines the corrected emission data from heads 22a, 22b, and 22c. More specifically, the combining circuitry combines data from each head representing the same ray. That is, the collimator 62 defines the path, relative to the head, along which radiation travelled to cause scintillation at the monitored location on the head. The location on the head and the angle of the head when the event was monitored define the ray or path between the corresponding emission source and the point of receipt.

The corrected emission projection data from the combining means 108 is stored in a total emission projection data memory 110. An emission data reconstruction processor 112 reconstructs the emission data into a corresponding three dimensional image representation which is stored in an emission image memory 114. A video display terminal 116 or other display means provides a man-readable display of the reconstructed emission distribution. Typically, various displays will be selected, such as transverse or lateral slices through the patient, or even a three dimensional prospective representation. An attenuation correction means 118 corrects the emission data $P_{km}$ from total emission projection data memory 110 for attenuation by iterative reconstruction algorithms or means and provides corrected emission projection data to the emission data reconstruction means.

Stated more mathematically, the emission projection data $P_{km}$ at projection angle $\Theta_m$ and detector bin or ray k, and the image or back projection value $X_{ij}$ at pixel (i,j) are defined as:

$$P_{km} = \Sigma_{ij} W_{ij}^{km} X_{ij} \quad (3a)$$

$$X_{ij} = \Sigma_{k,m} W_{ij}^{km} P_{km}, \quad (3b)$$

where the weighting factor $W_{ij}^{km}$ is given by $$W_{km}^{ij} = \frac{A_{ij}^{km}}{\mu_{ij}} (1 - e^{\mu_{ij} l_{ij}^{km}}) \quad \text{if } \mu_{ij} > 0. \quad (3c)$$

$$W_{ij}^{km} = l_{ij}^{km} A_{ij}^{km}, \quad \text{if } \mu_{ij} = 0, \quad (3d)$$

where $l_{ij}^{km}$ is the length of the ray through the pixel. The attenuation factor $A_{ij}^{km}$ is the exponential of the line integral of the attenuation coefficient $\mu_{ij}$ from $b_{ij}$, the entry point of projection ray to the pixel (i,j), to the detector. If no attenuation correction is needed, the attenuation coefficient $\mu_{ij}$ is set to be zero.

More specifically, the attenuation correction means 118 includes an attenuation factor calculating means 120 which calculates the attenuation factors $A_{ij}^{km}$. The attenuation factor calculating means calculates the exponential of the line integral of the scaled attenuation coefficients $\mu_{ij}$ along each ray k at angle $\Theta_m$ between pixel (i,j) and the detector head. Of course, zero values for rays that do not intersect the pixel need not be stored.

A weighting factor calculating means 122 calculates the weighting factors $W_{ij}^{km}$ in accordance with Equation (3c) for each emission data ray k and angle $\Theta_m$ and each pixel (i,j) of the emission distribution image memory 114. The calculated weighting factors are stored in an attenuation weighting factor memory or look-up table 124. The emission data reconstruction means 112 performs the multiplication and summing of Equation (3b) to generate the image values $X_{ij}$ at each iteration in accordance with the iterative scheme of Equation (4).

As in most reconstruction schemes, the subject region is divided into small pixels. For each pixel, an emission radionuclide concentration and a projection radiation attenuation coefficient are determined. These parameters can be estimated by maximizing the likelihood (probability of observations). The preferred algorithm includes a technique for computing maximum likelihood estimates. This algorithm has the unique ability to model the Poisson nature of photon counting and the physical differences between transmission and emission tomography. For SPECT, photon attenuation and variation of resolution with depth can be treated appropriately and the use of an accurate statistical model can improve the quality of reconstruction with low counts. The combination of good statistical and physical models should produce superior reconstructions. The preferred algorithm which the emission data reconstruction means 112 performs the EM iterative reconstruction algorithm, i.e.:

$$X_{ij}^{n+1} = \frac{X_{ij}^n}{\Sigma_{k',m'} W_{ij}^{k'm'}} \Sigma_{k,m} \left[ W_{ij}^{km} \frac{P_{km}}{P_{km}^n} \right]. \quad (4)$$

Figure 6:
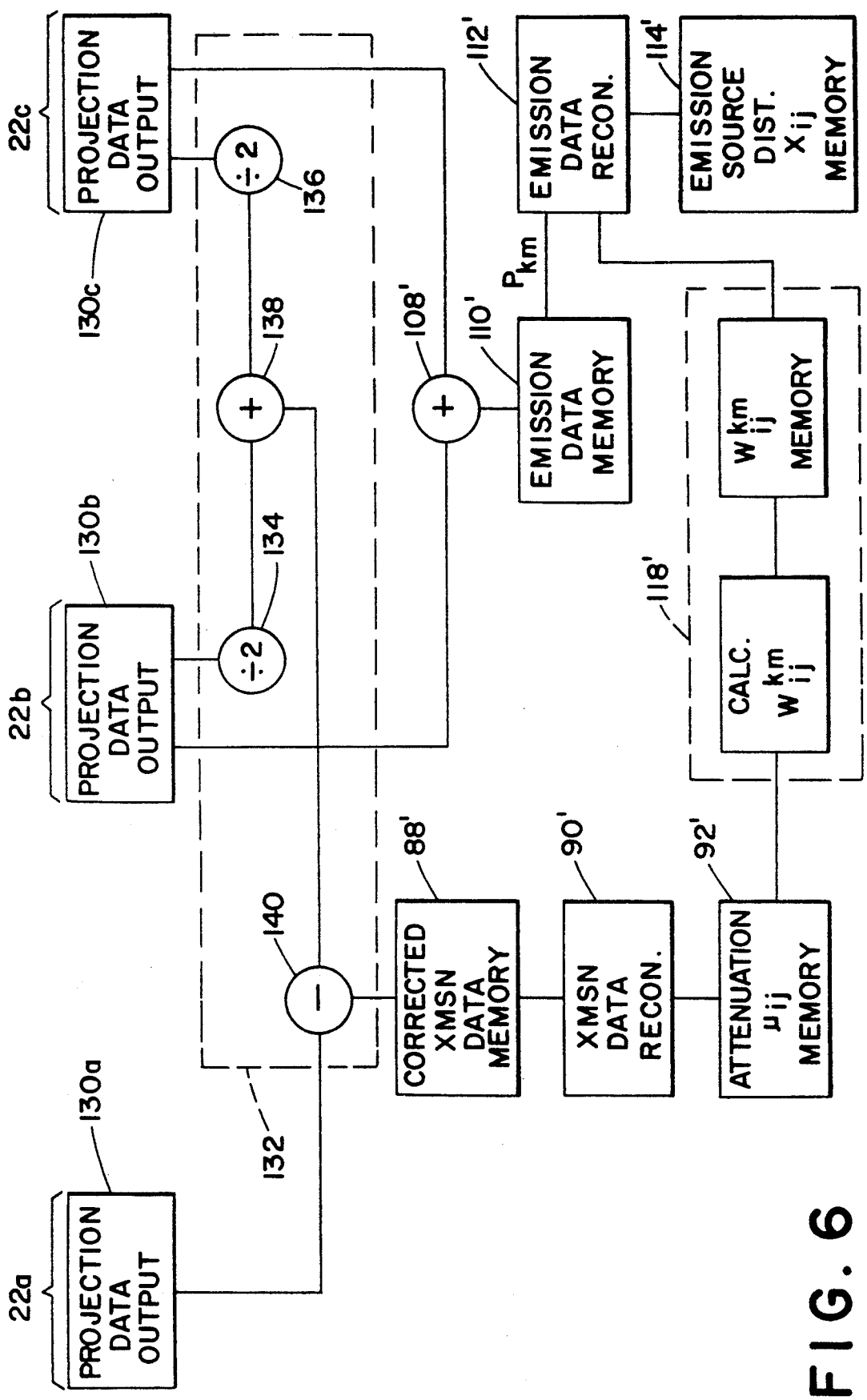
FIG. 6 illustrates the technique for processing emission and transmission data in the same energy range collected with the camera system of FIG. 1.

With reference to FIG. 6, the emission and transmission radiation may be sensed with the same energy range or window. Head 22a receives both the transmission and emission radiation; whereas, heads 22b and 22c receive the emission radiation. The heads 22a, 22b, and 22c have outputs 130a, 130b, and 130c, respectively, for outputting the common energy range radiation data. A transmission data correction means 132 corrects the data from output 130a in accordance with each emission data output from detector head outputs 130b and 130c. More specifically, the transmission data correcting means includes dividers 134 and 136 which divide the data from outputs 130b and 130c in half and an adding means 138 which combines the two halves to generate an average of the data received by the second and third heads. A subtraction means 140 subtracts the average data received by the second and third heads from the data received by the first head 22a to generate corrected transmission projection data which is stored in a corrected transmission data memory means 88'. A transmission data reconstruction means 90' reconstructs the corrected transmission data from the corrected data transmission memory means 88' to generate attenuation image data which is stored in an attenuation image memory means 92'.

An emission data combining means 108' combines emission data from the second and third heads and stores the emission data in an emission data memory means 110'. An attenuation correction means 118' corrects the emission data in accordance with the attenuation data as described above in conjunction with the two energy embodiment. An emission data reconstruction means 112' reconstructs the corrected emission data to generate an emission source distribution image which is stored in an emission source distribution memory means 114'.

With reference to FIG. 4B, more accurate gamma camera images can be reconstructed when the collimators focus on the region of interest to be imaged within the subject. Better emission images can be generated by moving the focal point of the collimators closer to the center of the patient. When the transmission radiation source is moved closer to the patient, part of the patient, at some angles, falls outside of the transmission fan, i.e. there is a truncation of part of the subject. The truncated region of the body tends to cause a ring artifact of analogous diameter around the reconstructed image.

One solution is to use different collimators on head 22a, that receives both emission and transmission radiation from heads 22b and 22c which receive only the emission radiation. That is, the emission only heads have collimators with a relatively short focal length, e.g. 50 cm., and the head 22a which receives both transmission and emission radiation has a longer focal length, e.g. 110 cm.

In another solution, the oval cross-section of a human patient which is only moderately truncated provides sufficient data to calculate the attenuation coefficient factors for the EM iterative construction algorithm and analogous algorithms to solve the transmission reconstruction problem as a solution to a system of linear equations. Even though the transmission image is distorted, the attenuation factors $A_{ij}^{km}$ (the exponentiation of the partial line integrals of the attenuation distribution $\mu_{ij}$) are measured accurate enough for those attenuation factors that have the greatest influence from the emission measurements.

Figure 7:
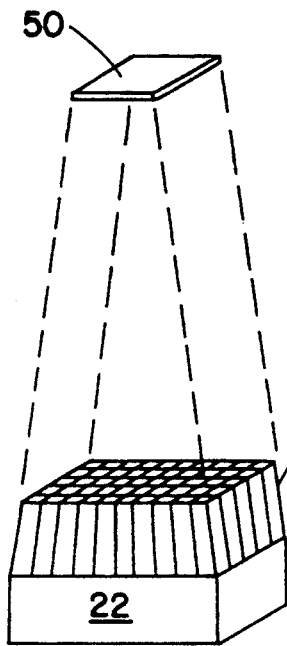
FIG. 7 is a diagrammatic illustration of an alternate embodiment using a rectangular bar transmission radiation source and a fan beam collimator.

With reference to FIG. 7, in an alternate embodiment, the transmission radiation source is a rectangular bar source which projects a fan beam or which is restricted to generate a fan beam of transmitted radiation toward a fan beam collimator mounted on the opposite detector head.

Figure 8:
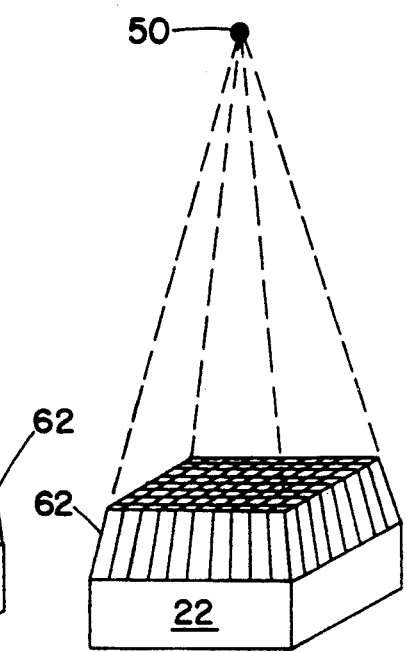
FIG. 8 is a diagrammatic illustration of a point transmission radiation source with a cone beam collimator.

With reference to FIG. 8, in another alternate embodiment, the radiation source is a point source which is restricted to direct a cone or pyramid of transmission radiation toward the oppositely disposed detector head. A cone beam collimator has tunnels which focus to a focal point at some distance from its surface.

Figure 9:
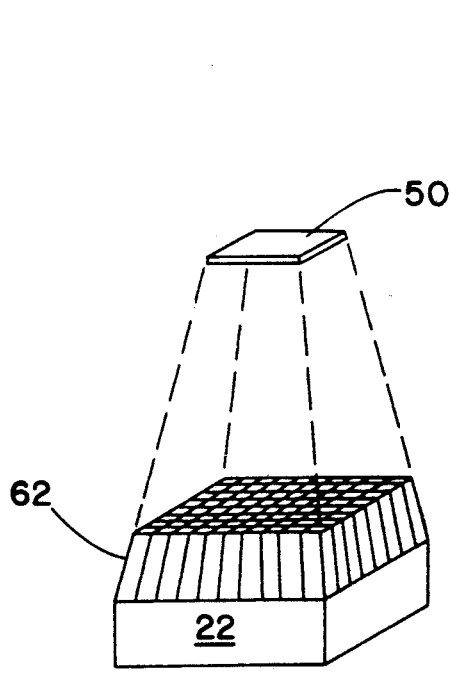
FIG. 9 is a diagrammatic illustration of a disk radiation source with a cone beam collimator.

In the alternate embodiment of FIG. 9, the radiation source is a small flat rectangular source or a disk source and the collimator a cone beam collimator.

Figure 10:
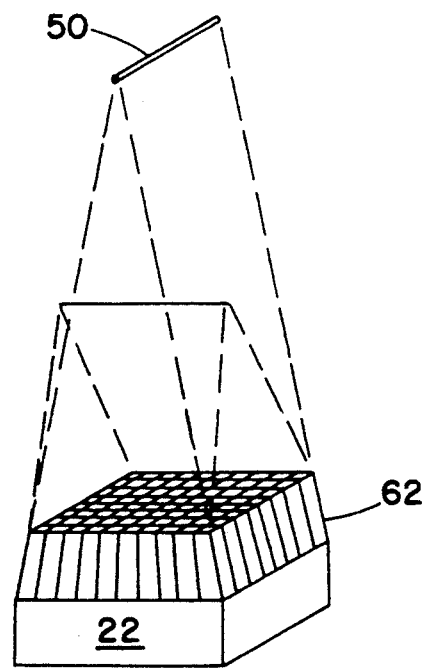
FIG. 10 is a diagrammatic illustration of a line radiation source with an astigmatic collimator.

With reference to FIG. 10, as yet another alternative, the transmission radiation source is a line source and an astigmatic collimator is used which places the focal point at two different focal lines. As yet another alternative, a flood source and a parallel collimator are used.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A gamma camera system comprising:
   three gamma camera heads disposed for movement around and facing an examination region, each gamma camera head receiving emission radiation from the examination region and producing output signals indicative thereof;
   a transmission radiation source disposed across the examination region and opposite from only a single one of the heads such that only one of the three gamma camera heads is disposed to receive both emission radiation from the examination region and transmission radiation directly from the source and two of the three gamma camera heads are disposed to receive emission radiation and only scattered transmission radiation from the examination region.

2. The gamma camera system as set forth in claim 1 wherein a subject in the examination region is injected with a radionuclide and further including:

a means for determining attenuation coefficients from the transmission radiation output signals from the head opposite the source;

a means for reconstructing an attenuation corrected image representation of radionuclide distribution from emission radiation signals from the heads.

3. A gamma camera system in which a subject in an examination region is injected with a radionuclide of at least a first energy level, the gamma camera system comprising:

three gamma camera heads disposed for movement around and facing the examination region; each gamma camera head receiving radiation from the examination region and producing output signals indicative thereof;

a transmission radiation source disposed opposite one of the heads across the examination region, the radiation source generating radiation of a second energy level;

each gamma camera head providing first and second energy level output signals; and a second energy level correcting means for correcting the second energy level signal from the head opposite the radiation source in accordance with other photopeak emission photons received by the other two camera heads, the second energy level output signal from each of the camera heads being connected with the second energy correction means.

4. A gamma camera head system comprising:

a plurality of gamma camera heads facing an examination region for receiving emission radiation emitted from a subject in the examination region;

a radiation source disposed across the examination region opposite one but not all of the heads such that the one head further receives transmitted radiation from the source which has traversed the examination region and at least one other head is positioned not across the examination region from a radiation source;

a circumferential moving means for moving the heads and the source circumferentially around the examination region;

a radial moving means for moving the heads toward and away from the examination region during the circumferential rotation;

a reconstruction means for processing concurrently received transmission radiation data from the one head and emission radiation data from the heads into an attenuation corrected image representation of emission radiation distribution in the examination region.

5. The gamma camera system as set forth in claim 4 further including:

a means for moving the radiation source toward and away from the examination region during the circumferential rotation;

a control means for controlling the radial moving means and the radiation source moving means such that the radiation source and the one head are maintained at a fixed spacing from each other.

6. The gamma camera system as set forth in claim 4 wherein the reconstruction means includes:

an attenuation data processing means for calculating attenuation correction values from the transmission radiation data;

an emission data processing means for reconstructing the corrected image representation from the attenuation correction values and the emission data.

7. A method of reconstructing emission projection signals from a three head gamma camera system to produce a pixelized image of a distribution of emission sources in an attenuating medium, the method comprising:

rotating the heads around the medium;

as the heads are rotated, simultaneously (i) transmitting radiation through the medium to one of the heads and (ii) receiving emission radiation from the emission sources distributed in the medium with the three heads and simultaneously collecting transmission and emission projection data;

determining cross-talk corrections from the simultaneously collected transmission and emission projection data to correct for transmission radiation contributions to the emission projection data and emission radiation contributions to the transmission projection data;

correcting the transmission and emission projection data with the cross-talk corrections;

generating attenuation coefficients from the transmission data for the pixelized space;

from the emission projection data set and the attenuation coefficient set, reconstructing an image space representation of the distribution of emission sources in the medium.

8. The method as set forth in claim 7 wherein in the step of transmitting radiation through the medium, the transmission radiation is one of x-rays from an x-ray tube and gamma radiation emanating from one of: a line source, a rectangular source, a point source, a disk source, and a flood source;

and further including the step of collimating radiation passing from the medium to the heads with at least one of: a fan beam collimator, a cone beam collimator, an astigmatic collimator, and a parallel collimator.

9. The method as set forth in claim 7 wherein the cross-talk correcting step includes correcting the transmission projection data for scatter and photopeak photons from multi-peak emission radionuclei.

10. The method as set forth in claim 9 wherein the emission and transmission sources having first and second energies, respectively, and wherein the step of correcting the transmission projection signals includes:

measuring first and second energy radiation photons with each of the three heads;

subtracting a portion of the transmission projection data from the transmission projection data of one of the heads to provide corrected transmission projection data;

reconstructing a corrected transmission image representation from the corrected transmission projection data, the attenuation coefficients being generated from the corrected transmission image representation.

11. The method as set forth in claim 7 wherein the transmission and emission radiation have substantially the same energy and wherein the step of correcting the transmission projection data for cross-talk includes:
   monitoring the emission projection data from the at least one head which is not across from the transmission radiation source;
   subtracting the monitored emission projection data from the simultaneously measured transmission and emission projection data of the head directly across from the transmission radiation source.

12. The method as set forth in claim 7 wherein the step of generating the attenuation coefficients for the pixelized space includes:
   correcting the emission projection data for scattered transmission radiation.

13. The method as set forth in claim 12 wherein the transmission and emission radiation have different energies and wherein the correcting step includes:
   measuring a portion of transmission and emission photons scattering into an emission energy range with the three heads;
   subtracting the measured portion from the measured emission projection data of the three heads to generate corrected emission projection data which are reconstructed into the emission source distribution representation.

14. The method as set forth in claim 12 wherein the transmission and emission radiation are of the same energy, and wherein the correction step includes:
   measuring a portion of the transmission and emission radiation in an emission energy range and detected by the two heads not directly opposite a transmission radiation source;
   subtracting the portion from the measured transmission projection data of the heads not opposite the radiation source to generate corrected transmission data for reconstruction into the attenuation coefficients.

15. A method of simultaneously measuring transmission and emission projection data, the method comprising:
   transmitting transmission radiation photons of a first energy from a radiation source on one side of an attenuating medium to a first gamma camera head disposed across the medium from the transmission radiation source;
   concurrently detecting the transmission radiation photons and emission radiation photons of a second energy from emission radiation sources distributed within the attenuating medium with the first camera head and concurrently detecting the emission radiation photons and scattered transmission radiation photons with at least one additional camera head;
   separating first and second energy photons received by the detector heads to generate first energy transmission projection data and second energy emission projection data;
   correcting the transmission projection data from the first detector head in accordance with the transmission projection data from the at least one additional camera head to correct for scatter;
   correcting the emission projection data in accordance with the corrected transmission projection data generated by the first head.

16. A method of simultaneously measuring transmission and emission photons from a subject, the method comprising:
   directing transmission radiation photons through the subject from a transmission radiation photon source;
   concurrently detecting transmission photons which have passed through the subject and emission photons emanating from emission sources distributed within the subject with a first camera head;
   concurrently detecting emission photons and scattered transmission photons with additional camera heads;
   correcting output data from (1) the first head with output data from the other heads and (2) the output data from the other heads with the output data from the first head.

17. A method of determining an emission source distribution within a subject, the method comprising:
   transmitting radiation photons through the subject;
   detecting only transmission radiation photons which have passed through a central portion of the subject such that transmission radiation photons passing through edge portions of the subject are not detected;
   determining radiation attenuation properties of the subject from the detected transmission radiation photons;
   concurrently with the detecting of transmission radiation photons, detecting emission radiation photons emitted by emission sources distributed within the central and edge portions of the subject;
   correcting (i) the determined radiation attenuation properties for contributions of the emission radiation photons and (ii) the detected emission radiation photons for contributions of the transmission radiation photons;
   from the corrected emission radiation photons, reconstructing a representation of the emission source distribution in the subject.

18. A gamma camera system for examining a subject in an examination region who has been injected with a radiopharmaceutical having a first characteristic energy level, the gamma camera system comprising:
   a transmission radiation source for generating radiation having a second characteristic energy level, the radiation source being disposed adjacent the examination region;
   a first gamma camera head disposed across the examination region from the radiation source such that the first gamma camera head receives radiation from the examination region of the first and second characteristic energy levels, the first gamma camera head generating first energy level and second energy level signals corresponding to a location on a face of the first gamma camera head at which radiation of the first and second energy levels, respectively, is received;
   at least a second gamma camera head mounted adjacent the examination region, the second gamma camera head being mounted with a face thereof facing toward the examination region and away from the transmission radiation source such that the second camera head receives radiation of the first characteristic energy level directly from the examination region and receives radiation of the second characteristic energy level from the examination region attributable to secondary photopeaks of the emission source and only scattered radiation from the transmission source and produces first energy level and second energy level signals indicative of a location on the second gamma camera head face at which radiation of the first and second energy levels, respectively, is received;

a means for rotating the first and second gamma camera heads and the transmission radiation source concurrently around the examination region;

a transmission radiation correction means for correcting the second energy level output signal of the first gamma camera head in accordance with the second energy level output signal of the second gamma camera head in order to correct for scatter and secondary photopeaks in the second characteristic energy range;

an emission radiation correcting means for correcting the first energy level signal from the first and second gamma camera heads in accordance with the corrected second energy level output signal; and a reconstruction means for concurrently processing corrected first and second energy level signals from the first and second gamma camera heads into at least an attenuation corrected image representation of emission radiation distribution in the examination region.

19. The gamma camera system as set forth in claim 18 further including a collimator mounted on the radiation receiving face of each gamma camera head, the collimator mounted to the first gamma camera head being one of:

a fan beam collimator;
a cone beam collimator;
an astigmatic collimator; and,
a parallel collimator.

20. The gamma camera system as set forth in claim 19 wherein the transmission radiation source includes one of:

a line source;
a bar source;
a point source;
a flat rectangular-shaped source which is small compared to an entrance surface of the collimator;
a disk source which is small compared to an entrance surface of the collimator; and,
a flood source.

21. The gamma camera system as set forth in claim 18 wherein the transmission radiation source includes one of an x-ray tube and a radionuclide.

22. The gamma camera system as set forth in claim 18 further including a source collimator means for restricting radiation from the transmission radiation source to impinge on the first head across the examination region therefrom.

23. The gamma camera system as set forth in claim 18 further including:

a means for moving the radiation source toward and away from the examination region.

24. The gamma camera system as set forth in claim 23 further including:

a radial moving means for moving the gamma camera heads radially toward and away from the examination region; and, a control means for controlling at least the radiation source moving means and the radial moving means such that the radiation source and the opposite head maintain a fixed spacing relative to each other.

* * * * *

UNITED STATES PATENT AND TRADEMARK OFFICE
CERTIFICATE OF CORRECTION

PATENT NO. : 5,210,421
DATED : May 11, 1993
INVENTOR(S) : Gullberg et al.

It is certified that error appears in the above-identified patent and that said Letters Patent is hereby corrected as shown below:

Column 1,
Line 1, please insert the paragraph:
-- The U.S. Government has a paid-up license in this invention and the right in limited circumstances to require the patent owner to license others on reasonable terms as provided by the terms of Grant No. R01 HL39792 awarded by the National Institute of Health. --

Signed and Sealed this

Eleventh Day of March, 2003

JAMES E. ROGAN
*Director of the United States Patent and Trademark Office*